United States Patent [19]
Shima et al.

[11] Patent Number: 6,162,946
[45] Date of Patent: Dec. 19, 2000

[54] PROCESSING FOR PRODUCING ALLYL 2-HYDROXYISOBUTYRATE

[75] Inventors: Yoshikazu Shima; Takafumi Abe, both of Niigata-ken, Japan

[73] Assignee: Mitsubishi Gas Chemical Company, Inc., Tokyo, Japan

[21] Appl. No.: 09/387,050

[22] Filed: Aug. 31, 1999

[30] Foreign Application Priority Data

Sep. 1, 1998 [JP] Japan .................................. 10-247282

[51] Int. Cl.$^7$ .................................................. C07C 69/66
[52] U.S. Cl. ............................................................ 560/179
[58] Field of Search ............................................. 560/179

[56] References Cited

U.S. PATENT DOCUMENTS

| | | |
|---|---|---|
| 2,355,330 | 8/1944 | Rehberg et al. . |
| 3,678,096 | 7/1972 | Trecker et al. . |
| 4,579,967 | 4/1986 | Linstid . |
| 5,480,954 | 1/1996 | Guo . |
| 5,519,103 | 5/1996 | Guo . |
| 5,605,995 | 2/1997 | Guo . |
| 5,639,827 | 6/1997 | Guo . |

*Primary Examiner*—James O. Wilson
*Assistant Examiner*—Robert W. Deemie
*Attorney, Agent, or Firm*—Antonelli, Terry, Stout & Kraus, LLP

[57] ABSTRACT

There is disclosed a process for producing allyl 2-hydroxyisobutyrate useful as a raw material for agrochemicals and pharmaceuticals, which comprises reacting methyl 2-hydroxyisobutyrate with allyl alcohol preferably by means of reactional distillation in the presence of a transesterification catalyst preferably comprising titanium tetramethoxide or titanium tetraisopropoxide under solventless mild reaction conditions including a reaction temperature in the range of 80 to 150° C. and a reaction time in the range of 10 minutes to 12 hours. The process enables efficient and easy production of the objective allyl 2-hydroxxyisobutyrate in high yield and high efficiency without the need of troublesome operations.

5 Claims, No Drawings

PROCESSING FOR PRODUCING ALLYL 2-HYDROXYISOBUTYRATE

BACKGROUND OF THE INVENTION

1. Field of the Invention

The present invention relates to a process for producing allyl 2-hydroxyisobutyrate in high efficiency by the use of methyl 2-hydroxyisobutyrate as a starting raw material. Allyl 2-hydroxyisobutyrate is employed as a raw material for pharmaceuticals and agrochemicals.

2. Description of the related Arts

As a process for producing allyl 2-hydroxyisobutyrate, there has heretofore been known a process for producing the same by using as starting raw materials, sodium 2-hydroxyisobutyrate and an allyl halide {refer to Zh. Org. Khim. 4 [3] (1968)}. However, the above-mentioned production process is intricate and troublesome in operation, since the sodium 2-hydroxyisobutyrate is in the form of a solid, and thus a solvent is usually indispensable in the reaction. In addition, said production process can not be said to be an industrially advantageous production process, since troublesome step is required to separate the solvent and a sodium halogenide.

SUMMARY OF THE INVENTION

Under such circumstances, the object of the present invention is to solve the aforesaid problems involved in the prior arts and at the same time, to provide an industrially advantageous process for producing allyl 2-hydroxyisobutyrate in high efficiency.

Other object of the present invention will become obvious from the content of this specification hereinafter disclosed.

In this connection, intensive extensive research and development were made by the present inventors in order to establish an industrially advantageous process for producing allyl 2-hydroxyisobutyrate. As a result, it has been found that high quality allyl 2-hydroxyisobutyrate is obtainable in high selectivity and at high yield by the reaction of methyl 2-hydroxyisobutyrate as a starting raw material with allyl alcohol in the presence of a transesterification catalyst. The present invention has been accomplished by the above mentioned findings and information.

Specifically, the present invention is concerned with a process for producing allyl 2-hydroxyisobutyrate which comprises reacting methyl 2-hydroxyisobutyrate with allyl alcohol in the presence of a transesterification catalyst.

DESCRIPTION OF THE PREFERRED EMBODIMENTS

In the following, some description will be given of the process for producing allyl 2-hydroxyisobutyrate according to the present invention. The methyl 2-hydroxyisobutyrate which is to be used as a starting raw material in the process according to the present invention may be produced by any of available methods, and preferably has a low water content and a low acid value. Preferably, it is produced by the method as disclosed in Japanese Patent Application Laid-open No. 290650/1989 (Hei-1) or 1718792/1993 (Hei-5), that is, by the reaction of 2-hydroxyisobutyric acid amide with methyl formate in the presence of a basic catalyst.

The water content in the starting raw liquid composed of methyl 2-hydroxyisobutyrate and allyl alcohol that are to be used in the process of the present invention is preferably at most 1000 ppm. A water content therein exceeding 1000 ppm interferes with the reaction to some extent. The acid value of the methyl 2-hydroxyisobutyrate to be used as the starting raw material in the process of the present invention is preferably at most 0.3 mg-KOH/g. An acid value thereof exceeding 0.3 mg-KOH/g interferes with the reaction to some extent.

Examples of the transesterification catalyst to be used in the process according to the present invention include organotin compounds such as dibutyltin oxide; organic titanates such as titanium tetramethoxide; organic sulfonic acids; and inorganic acids such as sulfuric acid. Of these, are preferable the organotin compounds and the organic titanates from the aspect of the catalyst recycling because of their easiness of separation from the objective product. In particular, the organic titanates are especially preferable taking into consideration that they have high solubility in the reaction liquid, do not bring about solid deposit and the like when the objective product is separated from the catalyst by means of distillation or the like even if the recovery rate thereof is enhanced, and thus facilitate the recovery of the catalyst and revitalization thereof. Moreover, titanium tetramethoxide is particularly preferable, since it has a valency of an ester group same as that of methanol which is by-produced in the process according to the present invention and thus prevents unnecessary impurities from being produced, thereby enabling the production of high quality allyl 2-hydroxyisobutyrate.

The reaction conditions of the process according to the present invention are selected in accordance with the type of the catalyst to be used therein and the like, and include a reaction temperature in the range of 20 to 200° C., preferably 80 to 150° C. and a reaction time in the range of 5 minutes to 24 hours, preferably 10 minutes to 12 hours. The molar ratio of allyl alcohol to methyl 2-hydroxyisobutyrate in the process according to the present invention needs only be in the range of 0.1 to 100, preferably 0.1 to 10 taking into consideration the cost of the energy required for the separation after the reaction.

In regard to the reaction system in the process according to the present invention, any of available systems may be adopted provided that the starting raw materials are brought into sufficient contact with the transesteritication catalyst. The transesterification, which is an equilibrium reaction, is effectively put into practice for the purpose of enhancing the conversion of the methyl 2-hydroxyisobutyrate by distilling away the by-produced methanol by means of reactional distillation or the like to the outside of the reaction system. The use of a solvent in the reaction is allowable as the case may be, but non use thereof is preferable, since said non use can dispense with the solvent recovery step after the reaction and at the same time, enhance the productivity per unit volume of the reaction system in the process according to the present invention.

By distilling the reaction liquid composed of allyl 2-hydroxyisobutyrate as it is which has been obtained in the above-mentioned manner, it is made possible to obtain allyl 2-hydroxyisobutyrate at a high yield as the objective product. The residual bottom product after the distillation as such is reused repeatedly as a transesterification catalyst without a special treatment or additional supply of a fresh catalyst.

To summarize the effects and advantages of the process according to the present invention, allyl 2-hydroxyisobutyrate as the objective product can be produced from methyl 2-hydroxyisobutyrate as a starting raw material under mild solventless reaction conditions in high efficiency and high yield by the use of a specific transesterification catalyst.

In the following, the present invention will be described in more detail with reference to working examples, which however shall not limit the present invention thereto.

EXAMPLE 1

A 300 ml three-necked flask equipped with a distillation tube, a thermometer and a stirrer was charged with 50 g (0.423 mol) of methyl 2-hydroxyisobutyrate having an acid value of 0.05 mg-KOH/g, and 50 g (0.862 mol) of allyl alcohol. The starting raw liquid consisting of the methyl 2-hydroxyisobutyrate and allyl alcohol had a water content of 300 ppm. Then, the flask was further charged with 0.6 g of titanium tetraisopropoxide as the transesterification catalyst. Subsequently the resultant mixture in the flask was reacted at a reaction temperature in the range of 95 to 130° C. for 4 hours and additional 4 hours making a total of 8 hours, while the by-produced methanol was distilled away outside the reaction system. As the results, the conversion of methyl 2-hydroxyisobutyrate was 65% for the reaction time of 4 hours, and 92% for the reaction time of 8 hours, and the selectivity to allyl 2-hydroxyisobutyrate was 99.9% for each reaction time.

EXAMPLE 2

The procedure in Example 1 was repeated to proceed with the reaction except that use was made of 50 g (0.423 mol) of methyl 2-hydroxyisobutyrate having an acid value of 0.41 mg-KOH/g (instead of 0.05 mg-KOH/g). The starting raw liquid consisting of the methyl 2-hydroxyisobutyrate and allyl alcohol had a water content of 300 ppm. Subsequently the resultant mixture in the flask was reacted in the same manner as in Example 1, but for 8 hours only. As the results, the conversion of methyl 2-hydroxyisobutyrate was 72%, and the selectivity to allyl 2-hydroxyisobutyrate was 99.9%.

EXAMPLE 3

The procedure in Example 1 was repeated to proceed with the reaction except that 0.3 g of titanium tetramethoxide instead of 0.6 g of titanium tetraisopropoxide was used as the transesterification catalyst, and that the reaction was carried out for 9 hours. As the results, the conversion of methyl 2-hydroxyisobutyrate was 91% and the selectivity to allyl 2-hydroxyisobutyrate was 99.9%.

EXAMPLE 4

The procedure in Example 1 was repeated to proceed with the reaction except that the starting raw liquid consisting of the methyl 2-hydroxyisobutyrate and allyl alcohol had a water content of 1400 ppm instead of 300 ppm, and that the reaction was carried out for 8 hours only. As the results, the conversion of methyl 2-hydroxyisobutyrate was 70%, and the selectivity to allyl 2-hydroxyisobutyrate was 99.9%.

EXAMPLE 5

The reaction liquid obtained in Example 2 was subjected as it is to vacuum distillation to obtain a major distill late at 107.5° C. and 100 mmHg ( 13.3 KPa ) which consisted essentially of allyl 2-hydroxyisobutyrate having a purity of not less than 99%. Subsequently the procedure in Example 1 was repeated to proceed with the reaction except that the residual solution in the bottom after the distillation was used as the transesterification catalyst instead of a fresh catalyst, and that the reaction was carried out for 8 hours only. As the results, the conversion to methyl 2-hydroxyisobutyrate was 92%, and the selectivity to allyl 2-hydroxyisobutyrate was 99.9%, which were same as the results for the reaction time of 8 hours in Example 1.

EXAMPLE 6

The procedure in Example 1 was repeated to proceed with the reaction except that 0.5 g of dibutyltin oxide was used as the transesteritication catalyst instead of 0.6 g of titanium tetraisopropoxide, and that the reaction was carried out for 4 hours only. As the results, the conversion of methyl 2 hydroxyisobutyrate was 55%, and the selectivity to allyl 2-hydroxyisobutyrate was 99.9%.

What is claimed is:

1. A process for producing allyl 2-hydroxyisobutyrate which comprises reacting methyl 2-hydroxyisobutyrate with allyl alcohol in the presence of a transesterification catalyst.

2. The process for producing allyl 2-hydroxyisobutyrate according to claim 1, wherein the transesterification catalyst is at least one member selected from the group consisting of organotin compounds and organic titanates.

3. The process for producing allyl 2-hydroxyisobutyrate according to claim 1, wherein the transesterification catalyst is at least one member selected from the group consisting of titanium tetramethoxide and titanium tetraisopropoxide.

4. The process for producing allyl 2-hydroxyisobutyrate according to claim 1, wherein the water content in the starting raw liquid comprising methyl 2-hydroxyisobutyrate and allyl alcohol is at most 1000 ppm.

5. The process for producing allyl 2-hydroxyisobutyrate according to claim 1, wherein the acid value of the methyl 2-hydroxyisobutyrate is at most 0.3 mg-KOH/g.

* * * * *